(12) United States Patent
Lubock

(10) Patent No.: US 6,923,754 B2
(45) Date of Patent: Aug. 2, 2005

(54) VACUUM DEVICE AND METHOD FOR TREATING TISSUE ADJACENT A BODY CAVITY

(75) Inventor: Paul Lubock, Laguna Niguel, CA (US)

(73) Assignee: SenoRx, Inc., Aliso Viejo, CA (US)

( * ) Notice: Subject to any disclaimer, the term of this patent is extended or adjusted under 35 U.S.C. 154(b) by 141 days.

(21) Appl. No.: 10/290,002

(22) Filed: Nov. 6, 2002

(65) Prior Publication Data

US 2004/0087827 A1 May 6, 2004

(51) Int. Cl.$^7$ .................................................. A61N 5/00
(52) U.S. Cl. .......................................................... 600/3
(58) Field of Search ............ 600/1–8; 604/590.1–591.1, 604/93.01, 96.01, 97.01, 101.01, 101.02–101.05, 103.01, 103.05, 103.06, 103.07

(56) References Cited

U.S. PATENT DOCUMENTS

| | | | |
|---|---|---|---|
| 5,106,360 A | 4/1992 | Ishiwara et al. | |
| 5,342,305 A | 8/1994 | Shonk | 604/101 |
| 5,417,687 A | 5/1995 | Nardella et al. | |
| 5,611,767 A | 3/1997 | Williams | 600/2 |
| 5,662,580 A | 9/1997 | Bradshaw et al. | |
| 5,863,285 A | 1/1999 | Coletti | 600/3 |
| 5,913,813 A | 6/1999 | Williams et al. | |
| 5,931,774 A | 8/1999 | Williams et al. | |
| 6,022,308 A | 2/2000 | Williams | |
| 6,083,148 A | 7/2000 | Williams | |
| 6,413,204 B1 | 7/2002 | Winkler et al. | |
| 6,458,069 B1 | 10/2002 | Tam et al. | 600/3 |
| 6,482,142 B1 | 11/2002 | Winkler et al. | |
| 6,673,006 B2 | 1/2004 | Winkler | |
| 2001/0049464 A1 | 12/2001 | Ganz | 600/1 |
| 2002/0045893 A1 | 4/2002 | Lane et al. | |
| 2002/0095114 A1 | 7/2002 | Palasis | 604/96.01 |

FOREIGN PATENT DOCUMENTS

WO    WO 02/09599    2/2002

OTHER PUBLICATIONS

International Search Report for PCT/US03/33775, mailed Mar. 16, 2004.

*Primary Examiner*—John P. Lacyk
(74) *Attorney, Agent, or Firm*—Edward J. Lynch; Duane Morris LLP

(57) ABSTRACT

Devices and methods are provided for applying vacuum near to devices for delivering treatments to tissue adjacent a body cavity, effective to draw adjacent tissue near to such devices and to enhance treatment of the tissue. Body cavities include natural body cavities and cavities remaining after removal of tissue such as cancerous tissue. A device may include an inner balloon assembly with an inflation conduit. A sheath assembly having a fluid-permeable sheath wall may enclose the inner balloon assembly. Vacuum applied to the space between the sheath and the inner balloon is useful to draw tissue into contact with the device, improving treatment effectiveness. Methods for treating tissue with such devices and systems are also provided. Treatments may include providing radioactive material for radiation treatment, providing chemotherapeutic material for chemotherapy, providing thermal treatment, and combinations thereof. Systems may include devices of the invention and a vacuum source.

25 Claims, 5 Drawing Sheets

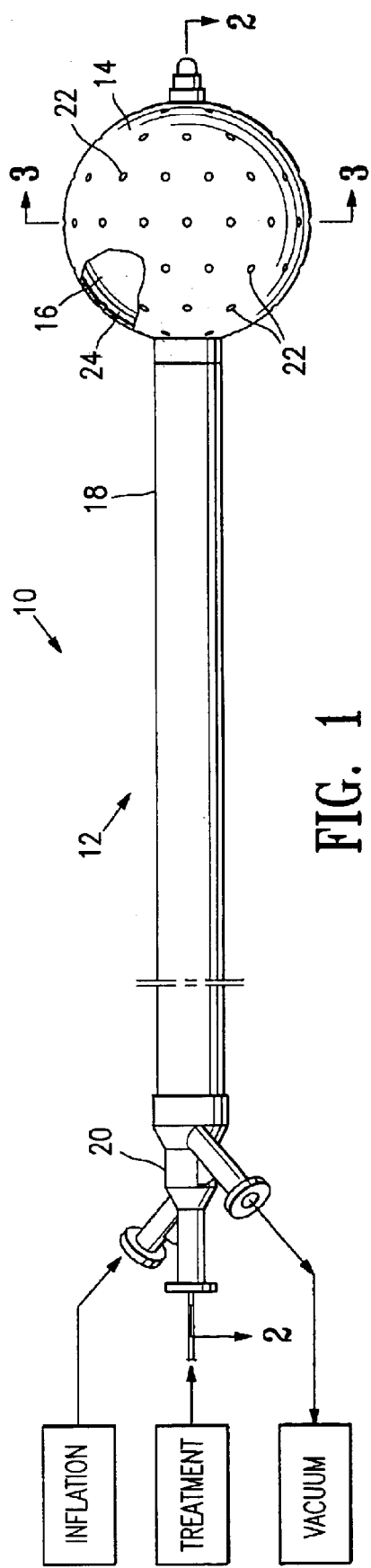
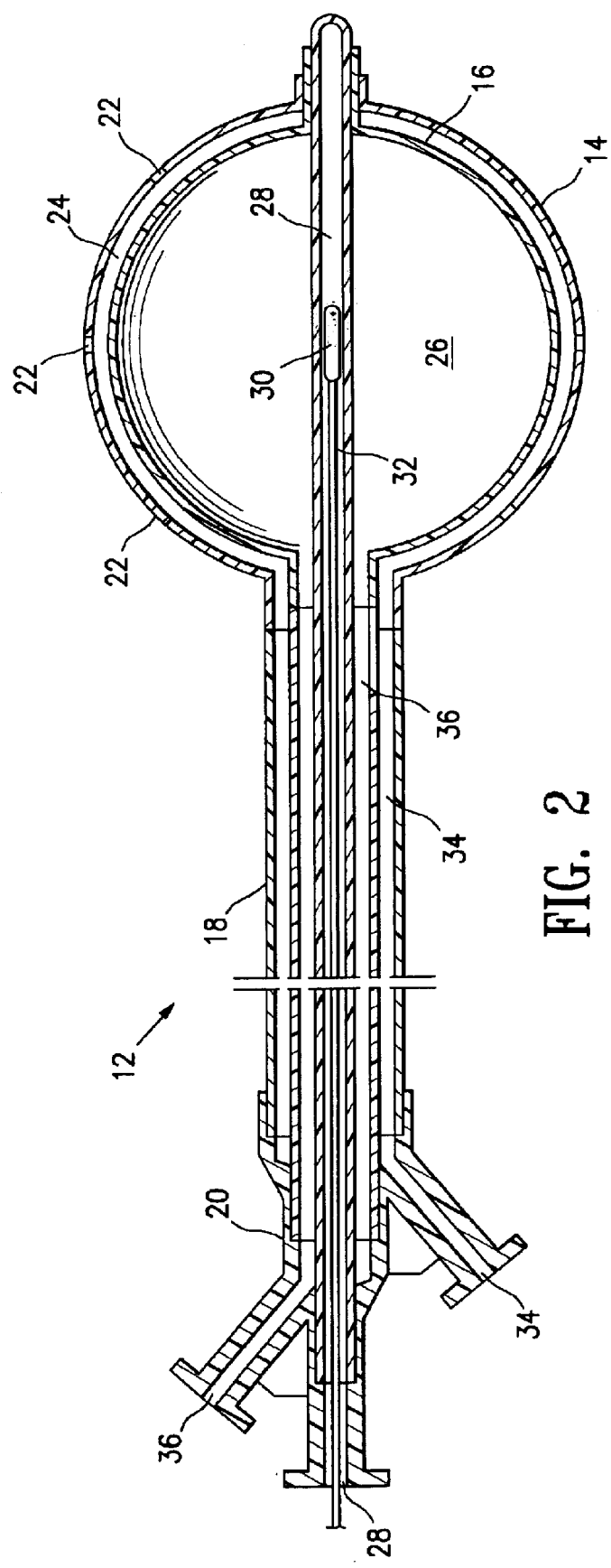

VACUUM DEVICE AND METHOD FOR TREATING TISSUE ADJACENT A BODY CAVITY

FIELD OF THE INVENTION

This invention relates generally to the fields of medical treatment devices and methods. In particular, the invention relates to devices and methods for treating tissue surrounding a body cavity, such as a site from which cancerous, pre-cancerous, or other tissue has been removed.

BACKGROUND OF THE INVENTION

In diagnosing and treating certain medical conditions, it is often desirable to perform a biopsy, in which a specimen or sample of tissue is removed for pathological examination, tests and analysis. A biopsy typically results in a biopsy cavity occupying the space formerly occupied by the tissue that was removed. As is known, obtaining a tissue sample by biopsy and the subsequent examination are typically employed in the diagnosis of cancers and other malignant tumors, or to confirm that a suspected lesion or tumor is not malignant. Treatment of cancers identified by biopsy may include subsequent removal of tissue surrounding the biopsy site, leaving an enlarged cavity in the patient's body. Cancerous tissue is often treated by application of radiation, by chemotherapy, or by thermal treatment (e.g., local heating, cryogenic therapy, and other treatments to heat, cool, or freeze tissue).

Cancer treatment may be directed to a natural cavity, or to a cavity in a patient's body from which tissue has been removed, typically following removal of cancerous tissue during a biopsy or surgical procedure. For example, U.S. Pat. No. 5,429,582 to Williams, U.S. Pat. No. 5,913,813 to Williams et al., U.S. Pat. No. 5,931,774 to Williams et al., U.S. Pat. No. 6,022,308 to Williams, U.S. Pat. No. 6,083,148 to Williams, and U.S. Pat. No. 6,413,204 to Winkler et al., the disclosures of which are all hereby incorporated by reference in their entireties, describe devices for implantation into a cavity resulting from the removal of cancerous tissue which can be used to deliver cancer treatments to surrounding tissue. One form of radiation treatment used to treat cancer near a body cavity remaining following removal of tissue is "brachytherapy" in which a source of radiation is placed near to the site to be treated.

Williams and coworkers describe implantable devices for treating tissue surrounding a cavity left by surgical removal of cancerous or other tissue that includes an inflatable balloon constructed for placement in the cavity. Such devices may be used to apply one or more of radiation therapy, chemotherapy, and thermal therapy to the tissue surrounding the cavity from which the tissue was removed. The balloon may be filled with a treatment fluid delivered via a conduit from a receptacle, syringe, or other means, or may receive a solid radiation source placed within the balloon. Thus, radiation treatment may be applied to tissue adjacent the balloon by placing radioactive material such as radioactive "seeds" within the balloon, or by filling the balloon with a liquid or slurry containing radioactive material. Multiple treatments may be applied simultaneously. For example, radioactive seeds may be placed within the balloon effective to irradiate tissue surrounding the balloon, and the balloon filled with a hot fluid at the same time to provide thermal treatment. After a suitable time, the hot fluid and/or the radioactive seeds may be removed. Such treatments, combined or otherwise, may be repeated if desired.

For example, a "MammoSite® Radiation Therapy System" (MammoSite® RTS, Proxima Therapeutics, Inc., Alpharetta, Ga. 30005 USA) includes a balloon catheter with a radiation source that can be placed within a tumor resection cavity in a breast after a lumpectomy. It can deliver a prescribed dose of radiation from inside the tumor resection cavity to the tissue surrounding the original tumor. The radiation source is typically a solid radiation source; however, a liquid radiation source may also be used with a balloon catheter placed within a body cavity (e.g., Iotrex®, Proxima Therapeutics, Inc.). The radiation source may be removed following each treatment session, or may remain in place as long as the balloon remains within the body cavity. Inflatable treatment delivery devices and systems, such as the MammoSite® RTS and similar devices and systems (e.g., GliaSite® RTS (Proxima Therapeutics, Inc.)), are useful to treat cancer in tissue adjacent a body cavity.

However, radiation, chemotherapy, thermal treatment, and other cancer treatments often have deleterious effects on healthy tissue in addition to the desired effects on cancerous tissue. In such treatments, care must be taken to direct the maximum treatment effects to diseased tissue while minimizing its delivery or effects on healthy tissue. For example, radiation treatment may be most effective when all surrounding tissue regions receive the same dose of radiation, and where the radiation dosage received by more distant tissue is as small and as uniform as possible. However, tissue cavities typically are not uniform or regular in their sizes and shapes, so that differences in dosages applied to different regions of surrounding tissue, including "hot spots" and regions of relatively low dosage, often result from radiation treatment.

Thus, there is need in the art for improved devices and methods for delivering cancer treatment to a cavity site within a patient's body.

SUMMARY OF THE INVENTION

The invention provides assemblies, devices, systems, and methods for treating tissue adjacent a body cavity, such as a cavity formed by the removal of tissue from a patient. In methods and devices having features of the invention, vacuum is applied effective to draw tissue towards a treatment assembly placed within the body cavity. Assemblies and devices embodying features of the invention include a vacuum delivery element configured to apply a vacuum. A vacuum delivery element may include a vacuum conduit, and may further include a vacuum port. A vacuum delivery element may be configured to at least partially surround or enclose a treatment assembly. A treatment assembly may be configured to deliver a treatment, such as radiation therapy, chemotherapy, thermal therapy, or other treatment, to tissue adjacent a body cavity. A treatment assembly may include a treatment delivery element configured to contain a treatment material, such as a radioactive source. A treatment assembly may include an inflatable balloon, which may be disposed at least in part around a treatment delivery element.

Assemblies and devices embodying features of the invention may include a vacuum delivery element such as a sheath or a balloon configured to provide vacuum effective to apply suction to tissue adjacent the assemblies and devices. Vacuum delivery elements are preferably configured to apply suction to tissue adjacent a treatment delivery assemblies, such as an inflatable treatment delivery device. Suction is effective to draw surrounding tissue close to the surface of a treatment assembly, or to a vacuum delivery element (such as a sheath or balloon) at least partially surrounding or enclosing a treatment assembly, so as to shape the tissue lining the body cavity for optimal treatment. Treatment may be by, e.g., radiation therapy, chemotherapy, thermal therapy, or other treatment modality supplied by the device. A treatment assembly may include an inflatable treatment assembly such as an inner balloon assembly configured to be at least partly enclosed by a vacuum delivery element such as a sheath or balloon. A sheath may be configured to at least partly enclose a balloon temporarily, following placement over or around an inner balloon. A balloon may be configured to at least partly enclose a balloon permanently following placement over or around an inner balloon.

Devices may further include an enclosure assembly (which may comprise a sheath assembly or a balloon assembly) comprising a vacuum conduit and a fluid-permeable enclosure wall (e.g., a sheath wall or a balloon wall) configured to partly or completely enclose an inner balloon assembly. Such an enclosure assembly may be effective to provide vacuum and a vacuum path to an intermediate space outside the inner balloon assembly. An intermediate space may include a space disposed between the inner balloon assembly and a sheath assembly or an outer balloon assembly. The enclosure assembly is preferably operatively connected to a vacuum conduit effective to provide vacuum to the intermediate space. Systems having features of the invention include such devices and further include a vacuum source configured to operatively connect with the vacuum conduit. In embodiments of devices having features of the invention, a fluid-permeable enclosure wall may have a hole or multiple holes configured to allow passage of fluid, may be made with a fluid-permeable material, such as a fluid-permeable woven material, or may be otherwise fluid-permeable. The space between the inner balloon and the enclosure may be prevented from collapse, even in the presence of suction from a vacuum delivered via the vacuum conduit, by separation elements disposed on the inner balloon wall, or on the enclosure wall, or both. In alternative embodiments, separation elements disposed within an intermediate space may be independent of both the inner balloon wall and the enclosure wall.

An embodiment of a device for treating tissue adjacent a body cavity having features of the invention further comprises an inner balloon assembly, which may include or be operatively connected with an inflation conduit configured to allow passage of a fluid. Devices may also have an inner balloon comprising a distensible inner balloon wall defining an internal lumen. Such an inner balloon may be operatively connected to an inflation conduit so as to allow for passage of fluid through an inflation conduit and into the internal lumen so as to inflate the inner balloon with the fluid.

An enclosure wall preferably comprises a flexible material, more preferably an elastic flexible material, although in embodiments of the invention, an eneclosure wall may comprise an inelastic flexible material. In embodiments of devices and systems having features of the invention, an enclsoure wall comprises a polymer, such as biocompatible polymer, preferably a radiation-resistant polymer. Suitable polymers include polyolefins such as polyethylene and polypropylene, polyurethanes, polyester, polyvinylchloride, polystyrene, thermoplastic polymers such as C-Flex® (Consolidated Polymer Technologies, Inc., Clearwater Fla. 33762), block polymers such as Kraton™ (Kraton Polymers, Houston Tex. 77208), an ionomer such as Surlyn® (Dupont, Wilmington Del. 19880), nylon, latex rubber, and silicon rubber (e.g., SILASTIC™, Dow Corning, Midland, Mich.).

Devices and systems having features of the invention include inner balloon assemblies configured to enclose a treatment material, such as radioactive material, chemotherapeutic agents, and thermal treatment materials (e.g., materials having a temperature greater than about 37° C.).

The invention further provides methods for treating tissue adjacent a body cavity, comprising contacting tissue adjacent a body cavity with a sheath or an outer balloon having a fluid-permeable wall of a device having features of the invention; and applying a vacuum effective to enhance the contact between the fluid-permeable wall and the tissue. Further methods may include delivering inflation fluid to an inner balloon lumen via an inflation conduit to inflate a distensible balloon. In embodiments of the methods of the invention, the inner balloon assembly comprises a treatment assembly such as a Mammosite RTS or similar inflatable treatment delivery device. Methods may include placing a treatment material within the device, and may further include replacing the treatment material.

Body cavities are typically not uniform in size or regular in shape. Devices, systems and methods having features of the invention utilize suction to draw tissue against the device surface within a body cavity, insuring good contact between the device and body tissue and providing control over the spacing between tissue and the device, including control over the distance from the treatment material contained within the devices. Tissue lining a body cavity that is held close to, or in contact with, devices having features of the invention forms a uniform and controlled surface, unlike tissue lining a body cavity in which a prior art treatment device has been merely inserted, but which does not urge tissue into a desired orientation and position. The control over the distance, spacing, and amount of tissue contact provided by devices, systems and methods of the present invention offer the advantages of improved treatment tissue adjacent a body cavity. Such improvements may include more uniform dosing, reduction of "hot spots," shorter treatments due greater correlation between desired and actual dosages, and reduction in the number of locations receiving inadequate dosages.

BRIEF DESCRIPTION OF THE DRAWINGS

FIG. 1 is partially cut-away perspective view of a system embodying features of the invention shown configured to deliver a treatment within a cavity in a patient's body tissue while providing vacuum effective to urge tissue into contact with an outer balloon surface.

FIG. 2 is a longitudinal cross-sectional view of the system of FIG. 1 taken along line 2—2.

DETAILED DESCRIPTION OF THE PREFERRED EMBODIMENTS

Figure 3:
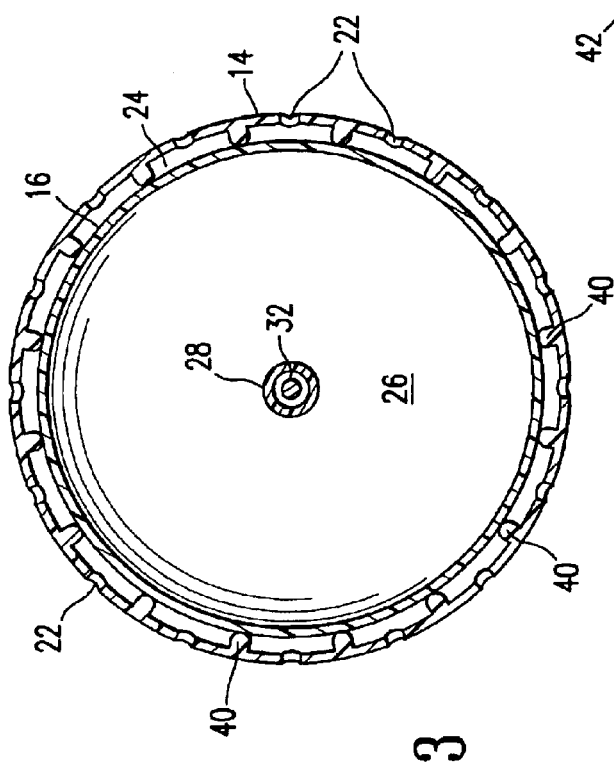
FIG. 3 is a transverse cross-sectional view of the system of FIG. 1 taken along line 3—3.

The present invention provides devices and methods for delivering a treatment, such as a cancer treatment, into a cavity within the body of an animal. For example, devices and methods having features of the invention may be used to deliver treatments into a biopsy site or into a cavity left after removal of cancerous tissue from within the body of a human patient. Vacuum is applied to tissue to enhance contact between a treatment delivery assembly within a body cavity and tissue surrounding the body cavity. A vacuum path around the treatment assembly is provided by devices, systems and methods embodying features of the invention. Vacuum may be applied to tissue via one, two, or multiple vacuum ports. A vacuum port may be a port in a vacuum delivery conduit, a hole in a sheath or balloon connected to a vacuum delivery conduit. A fluid permeable wall or portion of a fluid permeable wall may be effective to serve as a vacuum port.

FIG. 1 is a perspective view of a system 10 embodying features of the invention illustrating a device 12 having an outer balloon 14 enclosing an inner balloon 16 (shown in the cut-away portion of the illustration), a shaft 18 and connector 20. Outer balloon 14 comprises a sheath assembly around inner balloon 16. Outer balloon 14 is thus an example of an enclosure assembly, and forms an enclosure wall around inner balloon 16. Outer balloon 14 comprises at least in part a fluid permeable wall; as illustrated in FIG. 1, outer balloon 14 has holes 22 allowing fluid permeation into and out of balloon 14. In alternative embodiments, an outer balloon 14 may be made of woven or otherwise substantially continuous materials that are fluid permeable. In further embodiments, an enclosure wall or assembly such as an outer balloon may comprise a net, mesh, framework, or other discontinuous structure. Holes 22 (or fluid permeable material) allows fluids to pass through outer balloon 14 into intermediate space 24 disposed outside inner balloon 16. Intermediate space 24 provides a vacuum path adjacent inner balloon 16. Where at least a portion of outer balloon 14 is disposed adjacent inner balloon 16, intermediate space 24 is disposed between outer balloon 14 and inner balloon 16.

Inner balloon 16 defines an inner lumen 26, within which a delivery shaft 28 may be at least partially contained. As shown in FIG. 2, a treatment material 30 may be permanently or transiently disposed within delivery shaft 28. A probe 32 configured to move within delivery shaft 28 may be used to position treatment material 30, including to place treatment material 30 into and to retrieve placement material 30 from, within delivery shaft 28. A vacuum conduit 34 may be part of, or may be contained within, a shaft 18 and operatively connected to intermediate space 24. Shaft 18 may also include or contain an inflation conduit 36 configured to allow passage of inflation fluid into inner lumen 26. Passage of inflation fluid into inner lumen 26 is effective to inflate inner balloon 16. Inflation fluid may be any suitable fluid, either a gas or a liquid, and is typically inert. Inflation fluid, where a gas, may be, e.g., air, nitrogen, carbon dioxide or other gas. Inflation fluid, where a liquid, may be water, saline, mineral oil, or other liquid. In some embodiment, an inflation fluid may be effective to absorb radiation to, for example, moderate or adjust a dosage of radiation delivered to a patient's tissue from radioactive treatment material 30 contained within a delivery shaft 28.

Vacuum applied to intermediate space 24 is effective to deliver a treatment within a body cavity 38 within a patient's body effective to urge surrounding tissue into contact with at least a portion of the surface of the outer balloon 14.

The outer balloon 14 shown in FIGS. 1–5 is illustrated as a balloon that is configured to permanently or semi-permanently enclose inner balloon 16 or inner balloon assembly. Such an enclosure may be partial or complete. It will be understood that the outer surface of a device and of a system embodying features of the invention may also be a sheath 50 configured for deployment over and around an inner balloon assembly 14. In further embodiments, an enclosure may be, e.g. a net, mesh, framework, or other discontinuous structure.

FIG. 2 is a longitudinal cross-sectional view of the system of FIG. 1 taken along line 2—2 showing in cross section, for example, the relative positions of treatment material 30, an inner balloon 16, and an outer balloon 14 or sheath 50. FIG. 2 includes cross-sectional views of shaft 18 including views of delivery shaft 28, vacuum conduit 34 and inflation conduit 36. FIG. 3 is a transverse cross-sectional view of the system of FIG. 1 taken along line 3—3 showing outer balloon 14 and holes 22 therethrough, inner balloon 16 disposed within outer balloon 14, delivery shaft 28 and probe 32.

Figure 4B:
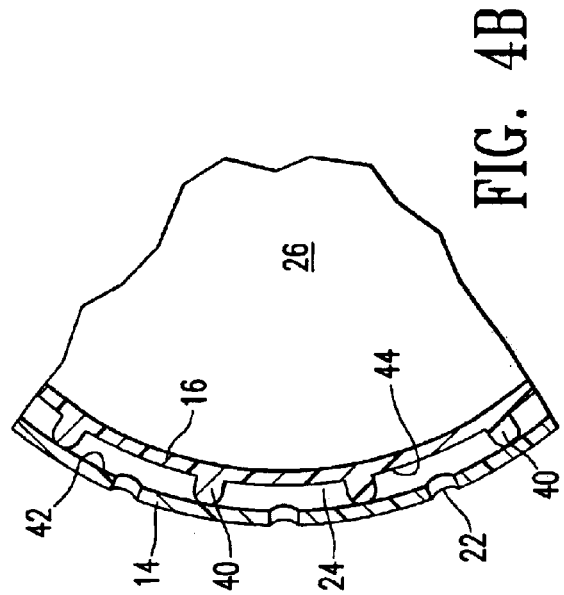
FIG. 4B is a cross-sectional view of the system of FIG. 1 showing a pie-shaped section of balloon walls between lines 4—4 for an embodiment in which an inner wall has stand-offs.
Figure 4A:
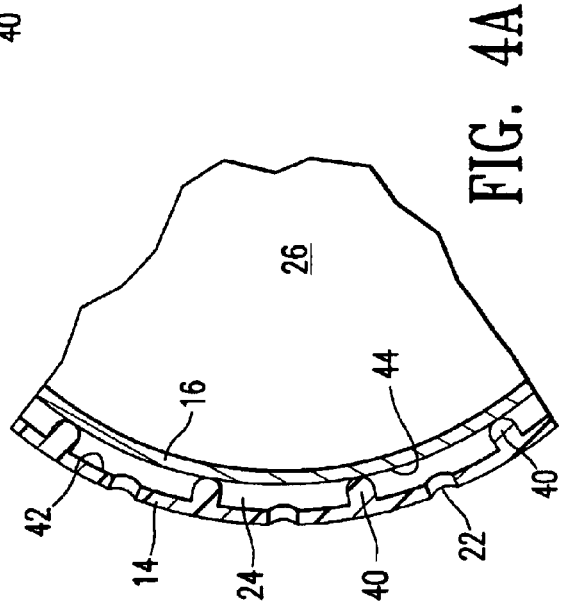
FIG. 4A is a cross-sectional view of a system of FIG. 1 showing a pie-shaped section of balloon walls between lines 4—4 for an embodiment in which an outer wall has stand-offs.

FIGS. 4A and 4B show portions of outer balloon 14 and inner balloon 16 as indicated in FIG. 1, including intermediate space 24 and spacers 40 which serve as separation elements effective to maintain patency of intermediate space 24 even under the influence of vacuum supplied via vacuum conduit 34. Spacers 40 may be part of outer balloon 14, or of inner balloon 16, or both. A spacer 40 may be a bump, knob, ridge, or other feature extending inwardly from an inner surface 42 of outer balloon 14, or extending outwardly from an outer surface 44 of outer balloon 14. In addition, or alternatively, a spacer 40 may be an object that is placed within intermediate space 24 and is separate from outer balloon 14 and inner balloon 16. For example, as shown in FIGS. 4A and 4B, spacers 40 may be stand-offs extending from an inner surface 42 of outer balloon 14 and from an outer surface 44 of outer balloon 14.

Figure 5A:
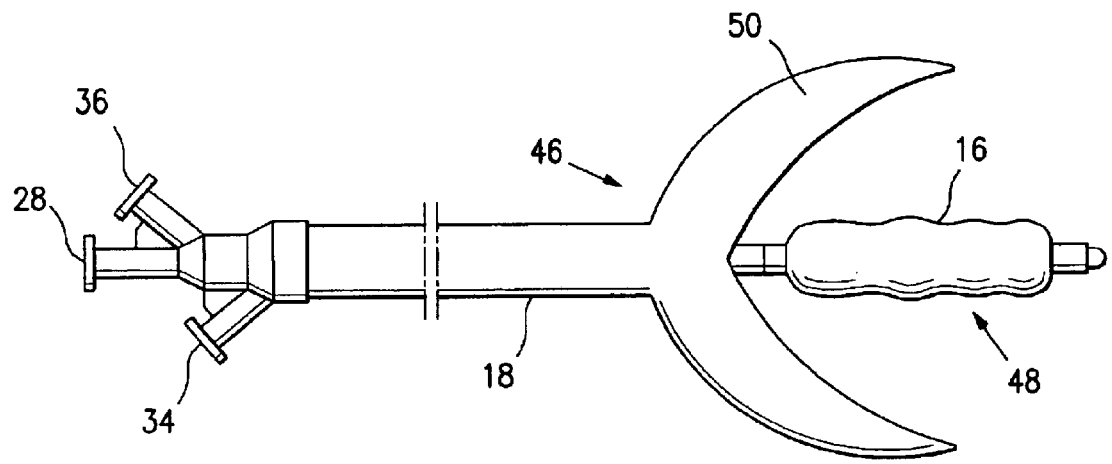
FIG. 5A shows a perspective view of a system embodying features of the invention in which an outer balloon assembly, in the form of a sheath, is being fitted over an inner balloon assembly.
Figure 5B:
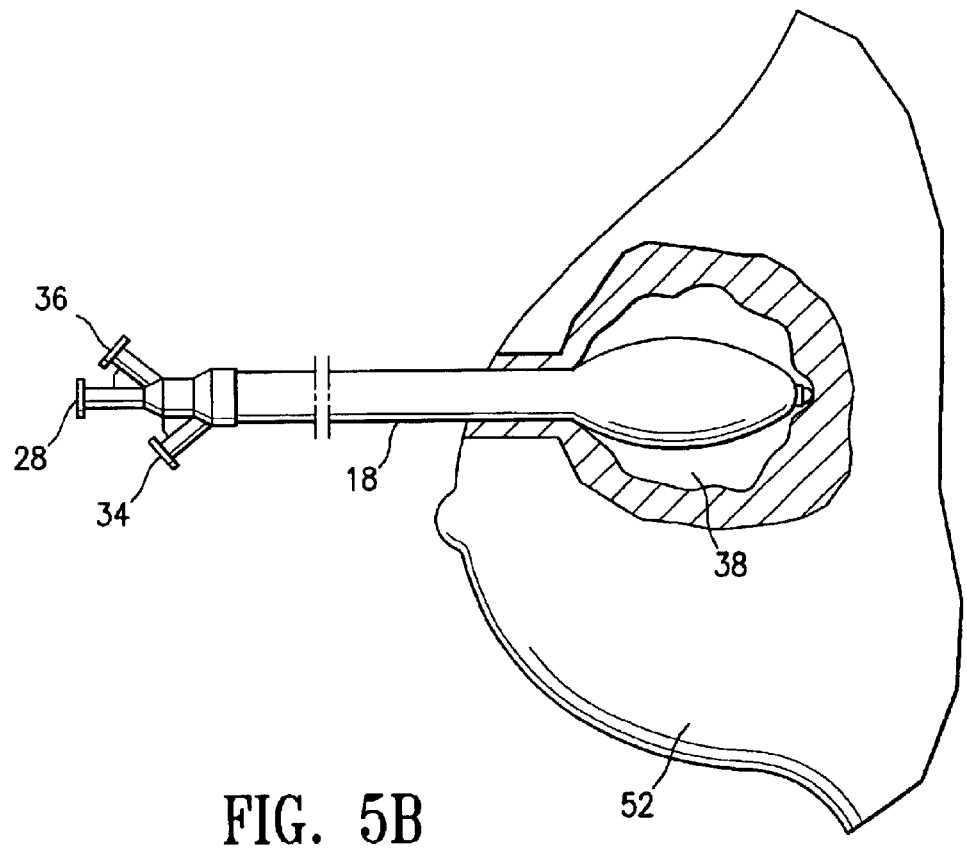
FIG. 5B shows a cross-sectional view of the assembled outer and inner balloon assemblies of FIG. 5A following placement into a cavity within a breast of a patient and before inflation of the inner balloon assembly.
Figure 5C:
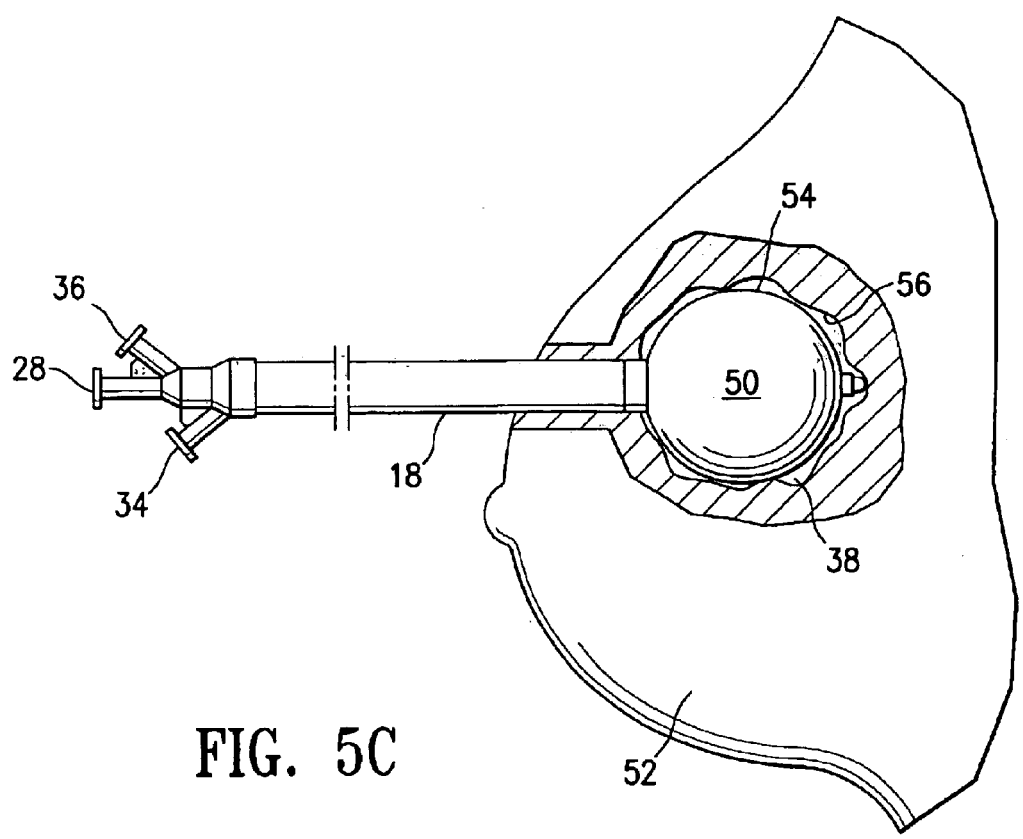
FIG. 5C shows a cross-sectional view of the assembled outer and inner balloon assemblies of FIG. 5A following inflation of the inner balloon assembly.

FIGS. 5A–5D illustrate the fitting of an outer balloon assembly 46 (including an outer balloon in the form of a sheath 50), over an inner balloon assembly 48 including an inner balloon 16. FIG. 5B shows the assembled outer 46 and inner 48 balloon assemblies of FIG. 6A following placement into a cavity 38 within a breast 52 of a patient and before inflation of the inner balloon assembly 48. In FIG. 5C, the inner balloon assembly 48 has been inflated by passage of inflation fluid through inflation conduit 36, pressing some parts of the outer surface 54 outer balloon assembly 46 into contact with portions of the inner surface 56 of body cavity 38. Note, however, that since most cavities 38 have irregular inner surfaces 56, there will typically be poor and intermittent contact between outer surface 54 of sheath 50 (or outer balloon 14 in alternative embodiments) and inner surface 56 of cavity 38, as shown in FIG. 5C.

Figure 5D:
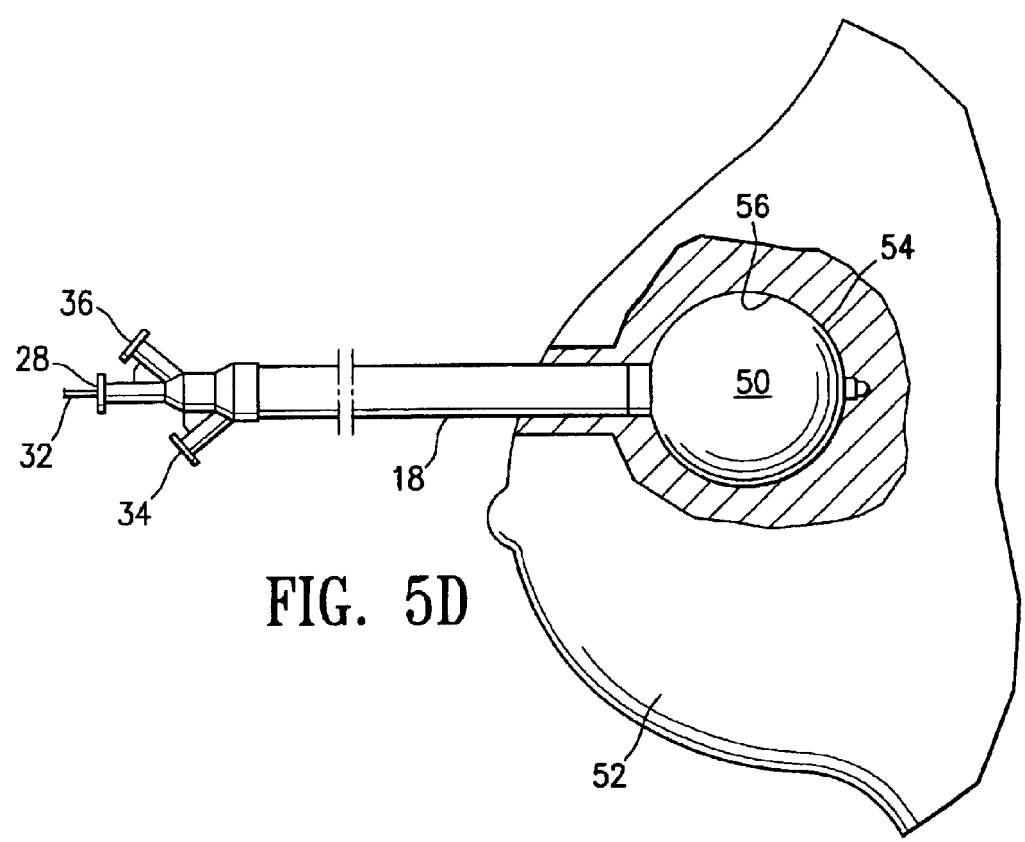
FIG. 5D shows a cross-sectional view of the assembled outer and inner balloon assemblies of FIG. 5A following application of vacuum to the lumen separating the inner balloon assembly and the outer balloon assembly, and after placement of a radioactive assembly within the inner balloon assembly.

FIG. 5D shows the assembled outer 46 and inner 48 balloon assemblies of FIG. 5A following application of vacuum via vacuum conduit 34 to the intermediate space 24 separating the inner balloon 16 and the sheath 50 (outer balloon 14). Treatment material 30 is in place within delivery shaft 28. Note that inner surface 56 of cavity 38 has been pulled into intimate contact with outer surface 54 of sheath 50. Such intimate contact configures inner surface 56 into an optimal configuration for the application of treatment by a treatment material 30. For example, radiation treatment by a radiation treatment material 30 is enhanced by proper positioning of adjacent tissue to provide proper irradiation. Irradiation levels may vary widely where the adjacent tissue of tissue cavity 38 is at different, irregular, or improper distances from a radiation source. Application of vacuum effective to draw tissue into better contact with device 12, e.g., into better contact with outer surface 54 of sheath 50, is effective to improve the delivery of radiation treatment from a radioactive treatment material 30.

Figure 6A:
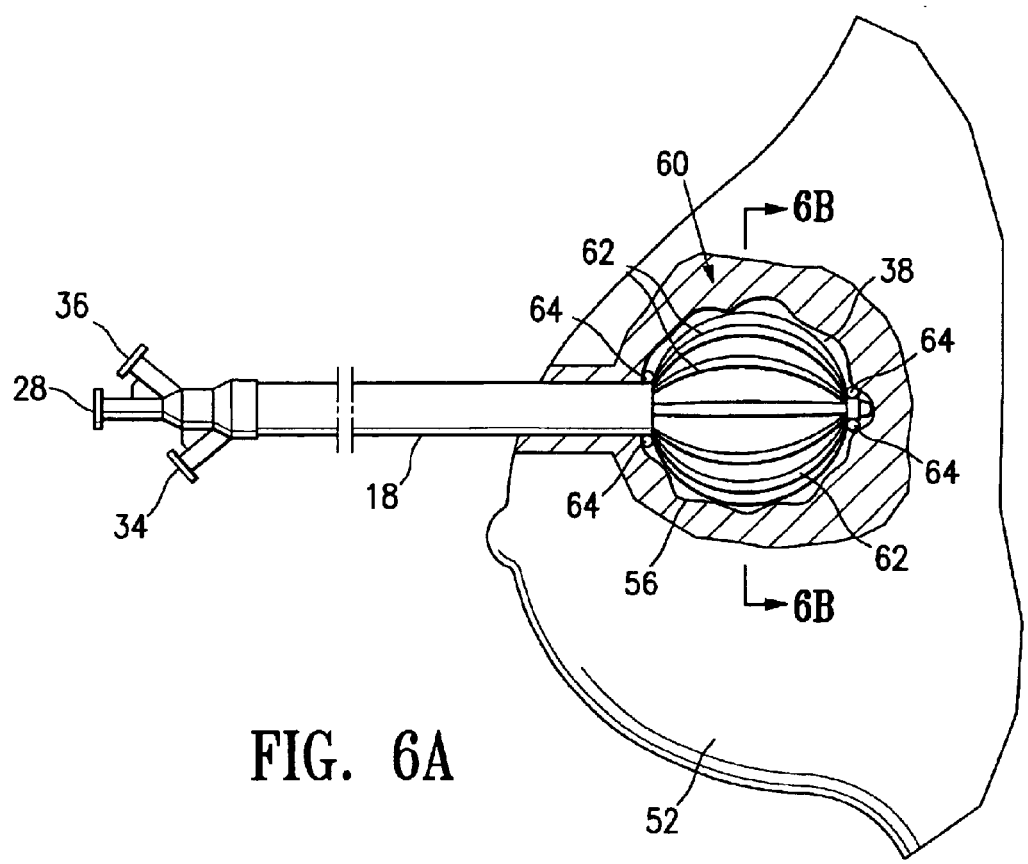
FIG. 6A is perspective view of a system embodying features of the invention including a vacuum delivery element configured to partly enclose an inner balloon assembly.
Figure 6B:
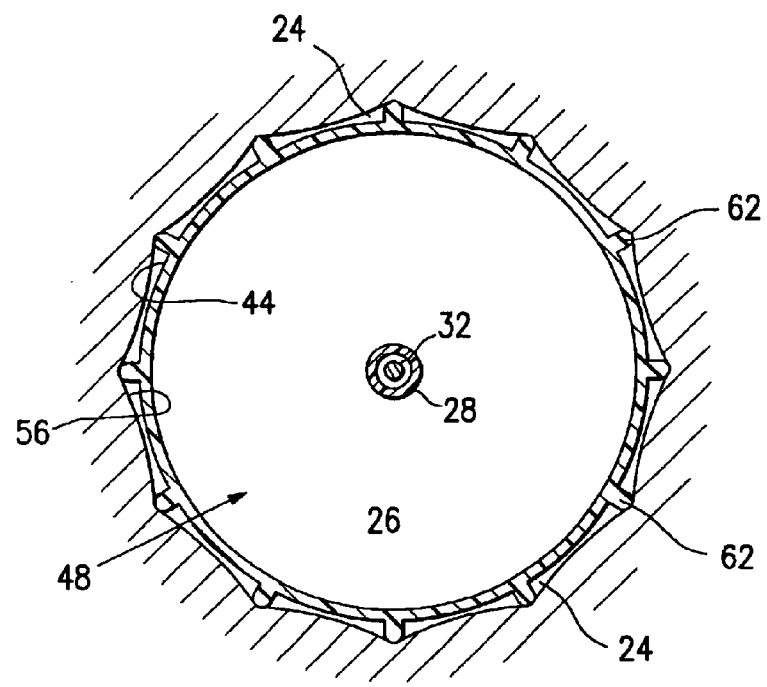
FIG. 6B is a cross-sectional view of the system of FIG. 6A taken along line 6B—6B.

FIG. 6A illustrates a system embodying features of the invention including a vacuum delivery element comprising an enclosure 60 having ribs 62 configured to partly enclose an inner balloon assembly 48. Vacuum is delivered to intermediate space 24 via vacuum ports 64 operatively connected to vacuum conduit 34. As shown in cross-section in FIG. 6B, ribs 62 serve as separation elements effective to provide vacuum paths in the intermediate space 24 between tissue surface 56 and outer surface 44 of inner balloon assembly 48.

Methods for treating tissue adjacent a body cavity 38 include methods for delivering a treatment to tissue adjacent a device 12 embodying features of the invention. For example, a method of treating tissue adjacent a body cavity 38 includes contacting tissue adjacent the body cavity 38 with a sheath 50 or an outer balloon 14, and applying a vacuum via vacuum conduit 34. The vacuum may be effective to draw adjacent tissue towards and into contact with a sheath 50 or an outer balloon 14, and so enhance the contact between the outer wall 54 and the tissue. Delivery of inflation fluid to an inner balloon 16 via an inflation conduit 36 to inflate inner balloon 16 is effective to enhance contact with adjacent tissue as well, serving to bring outer balloon 14 or sheath 50 closer to tissue than it would be in the absence of inflation of inner balloon 16. In preferred embodiments, the inner balloon assembly 48 comprises an inflatable treatment delivery device such as a Mammosite RTS (Proxima Therapeutics, Inc., Alpharetta, Ga. 30005) or similar device.

Methods further include placing a treatment material 30, such as a radiation source, within the device (e.g., by placement within a delivery shaft 28). A radiation source, such as a solid radiation source (e.g., a brachytherapy seeds) may be advanced into a delivery shaft 28 with a probe 32 or by other means. Other solid treatment materials 30 may similarly be advanced into a delivery shaft 28 with a probe 32 or by other means. A liquid radiation source (e.g., Iotrex®, Proxima Therapeutics, Inc., Alpharetta, Ga.) may be advanced into a delivery shaft 28 by fluid flow, under the influence of gravity, pressure applied by a syringe or other pressure source, or other means for delivering fluid into a space. Similarly, hot liquids and other liquid treatment materials 30 may be introduced into a delivery shaft 28 or an inner balloon 16 (via inflation conduit 36) under the influence of gravity, pressure applied by a syringe or other pressure source, or other means for delivering fluid into a space.

Some treatment regimens may include periodic or episodic treatment, in which radiation or other treatment is applied for a treatment period, and then the treatment is stopped for a recovery period. Such periodic or episodic treatments may be repeated, so that treatment is applied during a first treatment period, stopped during a first recovery period, and then treatment is re-applied for a second treatment period. Further treatment periods and recovery periods may also be used as necessary. Thus, methods may further include removal of a radiation source or other treatment material 30 from within a delivery shaft 28, and may further include replacing the treatment material 30.

Although a cavity 38 is typically an artificial cavity remaining after removal of tissue at biopsy, surgery, or other medical procedure, a body cavity may be a natural body cavity. For example, devices 12 may be inserted into a bladder for the treatment of bladder cancer. Application of suction is effective to enhance contact with a device 12 in such an example as well. Such enhanced contact may be effective to improve the delivery of radiation or other treatment, and may be effective to avoid "hot spots" (tissue regions receiving more radiation than is received by neighboring tissue regions) and is one of the important advantages provided by the present invention.

Treatment material 30 may include a chemotherapy agent effective to treat cancer or other disease condition of tissue surrounding a body cavity 38. In preferred embodiments, treatment material 30 includes a radiation source configured to delivery radiation to tissue adjacent a device 12.

Thus, treatment material 30 may include a radiation source which may be solid or liquid. A liquid radiation source may include, for example, a liquid containing a radioactive iodine isotope (e.g., $^{125}$I or $^{131}$I), a slurry of a solid isotope, e.g. $^{198}$AU, $^{90}$Y, $^{169}$Yb, or a gel containing a radioactive isotope. Liquid radiation sources are commercially available (e.g., Iotrex®, Proxima Therapeutics, Inc., Alpharetta, Ga.).

A solid radiation source may include brachytherapy seeds or other solid radiation source used in radiation therapy, such as, for example, a radioactive microsphere available from the 3M company of St. Paul, Minn. A solid radioactive source can either be preloaded into a device 12 at the time of manufacture or may be loaded into the device 12 after placement into body cavity 38 of a distal portion of the device 12. Such distal portion preferably includes the outer balloon 14, inner balloon 16, and at least a portion of delivery shaft 28. Such a solid radioactive core configuration offers the advantage in that it allows a wider range of radionuclides than if one is limited to liquids. Solid radionuclides suitable for use with a delivery device embodying features of the present invention are currently generally available as brachytherapy radiation sources (e.g., I-Plant™, Med-Tec, Orange City Iowa.).

In general, the amount of radiation desired by the physician is a certain minimum amount that is delivered to a site about 0–3 cm away from the wall of the body cavity 38 (e.g., from where a tumor has been excised). Vacuum applied to intermediate space 24 effects good contact between tissue surrounding body cavity 38 and the wall of the outer balloon 14 or sheath 50, promoting effective treatment delivery, such as delivery of radiation to surrounding tissue. It is desirable to keep the radiation in the region near the wall of the outer balloon 14 or sheath 50 as uniform as possible to prevent over-exposure to tissue at or near the reservoir wall. It is well known that the absorbed dose rate at a point exterior to a radioactive source is inversely proportional to the square of the distance between the radiation source and the target point. Thus, it is possible that the radiation dosage delivered to adjacent tissue may differ from that delivered to tissue disposed at more distal locations. In some instances, penetration of radiation to locations far from a device 12 is not desired. For example, in treating cancers such as bladder cancer, where the neoplastic tissue is generally located on the bladder surface, deep penetration is unnecessary and to be avoided.

An inflation fluid may also be a radiation absorbing fluid. For example, an inflation fluid may be an X-ray contrast agent as used in angiography, such as a Barium salt (e.g., barium sulfate), water, saline or other such fluid. A radiation-absorbing inflation fluid, which will surround a radiation source placed within delivery shaft 28, serves to moderate and control the delivery of radiation from the radiation source to surrounding tissue. Such moderation and control that is obtained with a radiation-absorbing inflation fluid may aid in avoiding the delivery of an excessive amount of radiation to some portions of the surrounding tissue.

Thus, in the absence of such a radiation-absorbing inflation fluid, it is possible in some instances that a radiation source sufficient to provide an effective dose at distances removed from a device 12, would expose tissue that is directly adjacent the wall of the outer balloon 14 or sheath 50 to an excessive radiation dose. Such excessive exposure to such tissue near to the device 12 may result in necrosis of healthy tissue necrosis.

Alternatively, an inflation fluid may contain radioactive elements, either as a liquid or slurry, so that the inner balloon 16 is filled with a source of radiation, providing a fairly uniform source of radiation that is distributed over the volume of the inner balloon 16. In such embodiments, an inflation fluid thus itself serves as a radiation source, thereby providing well-controlled amounts of radiation to surrounding tissue while minimizing irregularities in the dosages delivered to particular locations.

In embodiments of the invention in which an inflation fluid includes a radiation source, a delivery shaft 28 may contain a radiation absorptive material, so that, for example, less volume of radioactive material is required than if the entire volume of a device 12 were filled with radioactive material. Such a configuration may be advantageous where a profile exhibiting higher intensity at a tissue surface with lesser penetration is desired. Moreover, the outer balloon 14 need not be spherical, yet a uniform profile of radiation delivery is obtainable. Experiments reported in Williams U.S. Pat. No. 5,918,813 are described as showing that a steeper radial absorbed source gradient can be obtained using a radiation attenuation fluid in an inner chamber of a similar radiation deliver device than otherwise obtains with a device having only a single distensible chamber (as described in Williams U.S. Pat. No. 5,429,582).

What is claimed is:

1. A device for treating tissue adjacent a body cavity, comprising:
   a. an elongated shaft having proximal and distal portions and having an inflation lumen, a vacuum lumen and a therapeutic agent delivery lumen in at least a distal portion of the shaft;
   b. an inner balloon assembly having a distensible inner balloon wall defining an interior chamber in fluid communication with the inflation lumen so as to allow for passage of inflation fluid through the inflation lumen into the interior chamber;
   c. a receptacle within the interior chamber of the inner balloon wall in fluid communication with the therapeutic agent delivery lumen and configured to receive a therapeutic agent therefrom; and
   d. an outer sheath assembly having a fluid-permeable sheath wall enclosing at least in part the inner balloon wall and defining an intermediate space between the inner balloon wall and the sheath wall and configured to be in fluid communication with the vacuum lumen and provide vacuum to the intermediate space.

2. The device for treating tissue adjacent a body cavity of claim 1, wherein said fluid-permeable sheath wall has at least one hole therethrough.

3. The device for treating tissue adjacent a body cavity of claim 1, wherein said fluid-permeable sheath wall is formed at least in part of a fluid-permeable material.

4. The device for treating tissue adjacent a body cavity of claim 3, wherein said fluid-permeable material is a woven material.

5. The device for treating tissue adjacent a body cavity of claim 1, wherein separation elements are disposed between the sheath wall and the inner balloon wall.

6. The device for treating tissue adjacent a body cavity of claim 1, wherein separation elements are on an outer surface of the inner balloon wall.

7. The device for treating tissue adjacent a body cavity of claim 1, wherein said sheath wall is formed at least in part of a flexible material.

8. The device for treating tissue adjacent a body cavity of claim 7, wherein said sheath wall is formed at least in part of an elastic flexible material.

9. The device for treating tissue adjacent a body cavity of claim 8, wherein said sheath wall is formed at least in part an inelastic flexible material.

10. The device for treating tissue adjacent a body cavity of claim 1, wherein said sheath wall is formed at least in part of a polymeric material.

11. The device for treating tissue adjacent a body cavity of claim 10, wherein the polymeric material is a biocompatible polymer.

12. The device for treating tissue adjacent a body cavity of claim 10, wherein the polymeric material is at least in part a radiation-resistant polymer.

13. The device for treating tissue adjacent a body cavity of claim 10, wherein the polymeric material is selected from the group of polymers consisting of a polyolefin, polyethylene, polypropylene, polyurethane, polyester, polyvinylchloride, polystyrene, nylon, latex rubber, silicon rubber, a thermoplastic polymer.

14. The device for treating tissue adjacent a body cavity of claim 1, wherein the treatment lumen is configured to deliver a treatment agent within the interior chamber defined by the inner balloon wall.

15. The device for treating tissue adjacent a body cavity of claim 14, wherein the treatment agent is selected from the group consisting of radioactive material, chemotherapeutic agents, and materials having a temperature greater than about 37° C.

16. The device for treating tissue adjacent a body cavity of claim 1, wherein the sheath wall forms an outer balloon wall disposed about the inner balloon wall.

17. The device for treating tissue adjacent a body cavity of claim 16, wherein the outer balloon wall is formed at least in part of a polymeric material.

18. The device for treating tissue adjacent a body cavity of claim 17, wherein the polymeric material is selected from the group of polymers consisting of a polyolefin, polyethylene, polypropylene, polyurethane, polyester, polyvinylchloride, polystyrene, nylon, latex rubber, silicon rubber, a thermoplastic polymer.

19. The device for treating tissue adjacent a body cavity of claim 16, wherein the outer balloon wall is configured to enclose a treatment agent.

20. The device for treating tissue adjacent a body cavity of claim 19, wherein the treatment agent is selected from the group consisting of radioactive material, chemotherapeutic agents, and materials having a temperature greater than about 37° C.

21. The device of claim 1, wherein outer sheath is at least in part fluid permeable.

22. The device of claim 1, wherein said treatment agent is a material selected from the group consisting of radioactive material, chemotherapeutic agents, and thermal treatment materials.

23. The device for treating tissue adjacent a body cavity of claim 1, wherein separation elements are on an inner surface of the sheath.

24. A system for treating tissue adjacent a body cavity, comprising:
   a. an elongated shaft having proximal and distal portions and having an inflation lumen, a vacuum lumen and a therapeutic agent delivery lumen in at least a distal portion of the shaft;
   b. an inner balloon assembly having a distensible inner balloon wall defining an interior chamber in fluid communication with the inflation lumen so as to allow for passage of inflation fluid through the inflation lumen into the interior chamber;
   c. an outer sheath assembly having a fluid-permeable sheath wall enclosing at least in part the inner balloon wall defining an intermediate space between the inner balloon wall and the sheath wall and configured to be in fluid communication with the vacuum lumen and provide vacuum to the intermediate space; and
   d. a vacuum source operatively configured to be in fluid communication with the vacuum lumen.

25. A method for treating tissue defining at least in part a body cavity, comprising:
   a. providing a device having an elongated shaft with an inflation lumen, a vacuum lumen and a therapeutic agent delivery lumen, an inflatable inner balloon member in fluid communication with the inflation lumen, a fluid permeable outer sheath surrounding at least part of the inner balloon member and in fluid communication with the vacuum lumen and a receptacle configured to receive a therapeutic agent through the therapeutic agent delivery lumen;
   b. inserting the device into the body cavity;
   c. inflating the inner balloon within the body cavity;
   d. providing a therapeutic agent within the receptacle provided in the interior of the inner balloon;
   e. applying a vacuum to the interior of the outer sheath to engage tissue defining the body cavity.

* * * * *